(12) United States Patent
Hess et al.

(10) Patent No.: US 8,337,442 B2
(45) Date of Patent: Dec. 25, 2012

(54) ANKLE JOINT ORTHOSIS

(75) Inventors: Heinrich Hess, Kleinblittersdorf (DE);
Rainer Scheuermann, Rainsdorf (DE);
Wolfgang Krause, Hofbieber (DE)

(73) Assignee: Bauerfeind AG, Zeulenroda (DE)

( * ) Notice: Subject to any disclaimer, the term of this patent is extended or adjusted under 35 U.S.C. 154(b) by 599 days.

(21) Appl. No.: 12/439,982

(22) PCT Filed: Sep. 5, 2007

(86) PCT No.: PCT/EP2007/007731
§ 371 (c)(1),
(2), (4) Date: Dec. 1, 2009

(87) PCT Pub. No.: WO2008/028643
PCT Pub. Date: Mar. 13, 2008

(65) Prior Publication Data
US 2010/0106066 A1    Apr. 29, 2010

(30) Foreign Application Priority Data
Sep. 5, 2006 (DE) .......................... 10 2006 041 195

(51) Int. Cl.
*A61F 5/00* (2006.01)
(52) U.S. Cl. ............. 602/27; 602/23; 128/882; D24/192
(58) Field of Classification Search ................ 602/5, 23, 602/27; D24/192; 128/869, 882
See application file for complete search history.

(56) References Cited

U.S. PATENT DOCUMENTS

| 4,981,132 | A |   | 1/1991  | Chong |
| 4,982,733 | A | * | 1/1991  | Broadhurst et al. ............ 602/27 |
| 5,069,202 | A | * | 12/1991 | Prock ............................... 602/27 |
| 5,209,722 | A | * | 5/1993  | Miklaus et al. ................. 602/27 |
| 5,472,411 | A |   | 12/1995 | Montag et al. |
| 6,053,884 | A | * | 4/2000  | Peters ............................. 602/27 |
| 2004/0034316 | A1 |   | 2/2004 | Castro |

FOREIGN PATENT DOCUMENTS

| DE | 27 44 445 A1 | 4/1979 |
| DE | 86 17 783 U1 | 1/1987 |
| DE | 90 04 108.9 U1 | 6/1990 |
| DE | 91 02 013.1 U1 | 6/1992 |
| DE | 41 12 069 A1 | 10/1992 |
| DE | 43 18 588 C1 | 8/1994 |
| DE | 690 08 342 T2 | 11/1994 |
| DE | 298 00 441 U1 | 4/1998 |
| WO | WO-98/29060 A | 7/1998 |

* cited by examiner

*Primary Examiner* — Loan Thanh
*Assistant Examiner* — Camtu Nguyen
(74) *Attorney, Agent, or Firm* — Birch, Stewart, Kolasch & Birch, LLP

(57) ABSTRACT

The invention relates to an ankle orthosis comprising a U-shaped support stirrup made of a flexible material, the sides of which stirrup converge beneath the foot in a web projecting as a tab toward the metatarsus, extend past the bones, and are held together at their end regions by a fastening strap wrapping around the leg. The tab has a convexity, which presses against the cuboid bone of the foot due to a preloading of the tab.

17 Claims, 3 Drawing Sheets

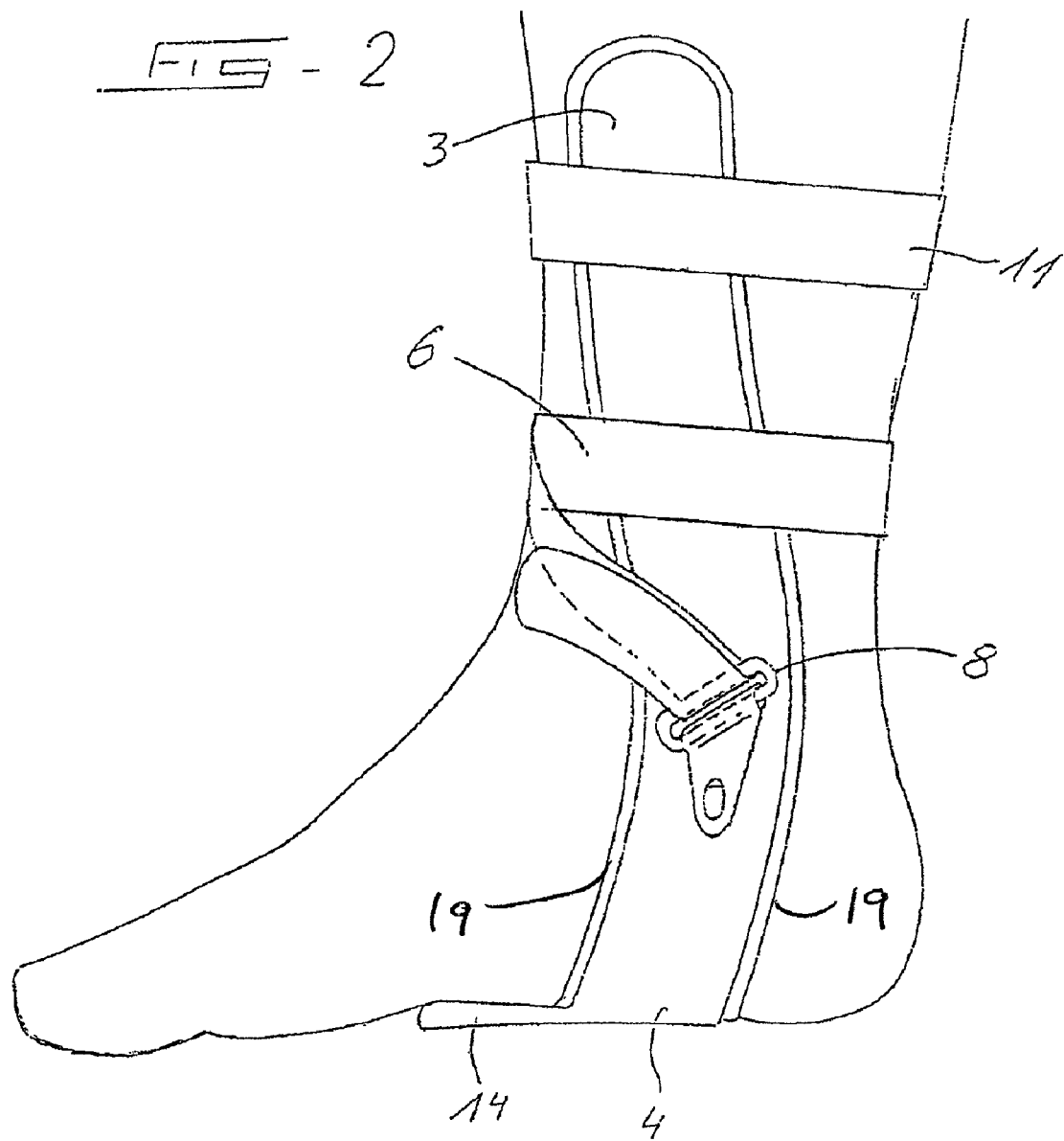

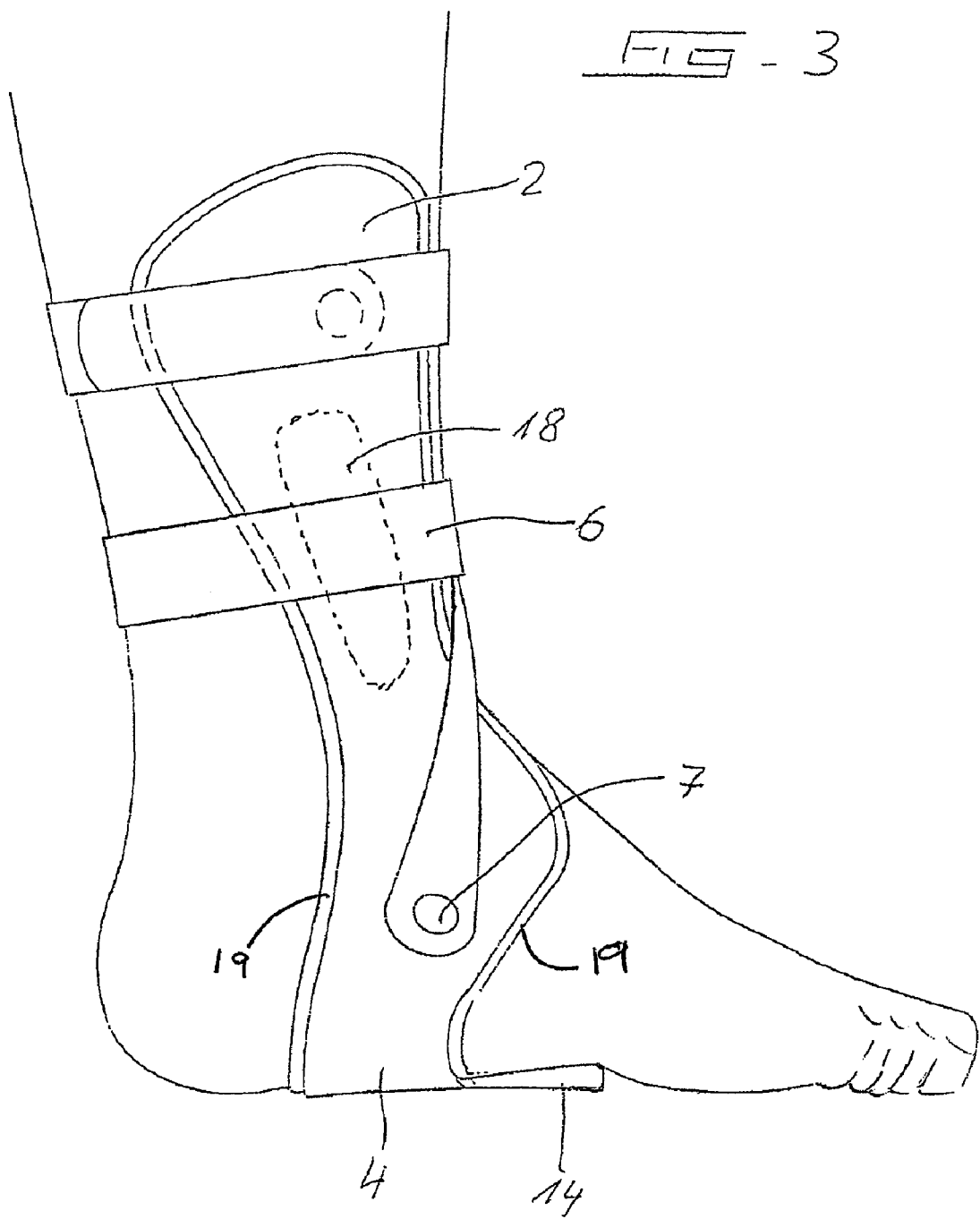

ANKLE JOINT ORTHOSIS

Figure 1:
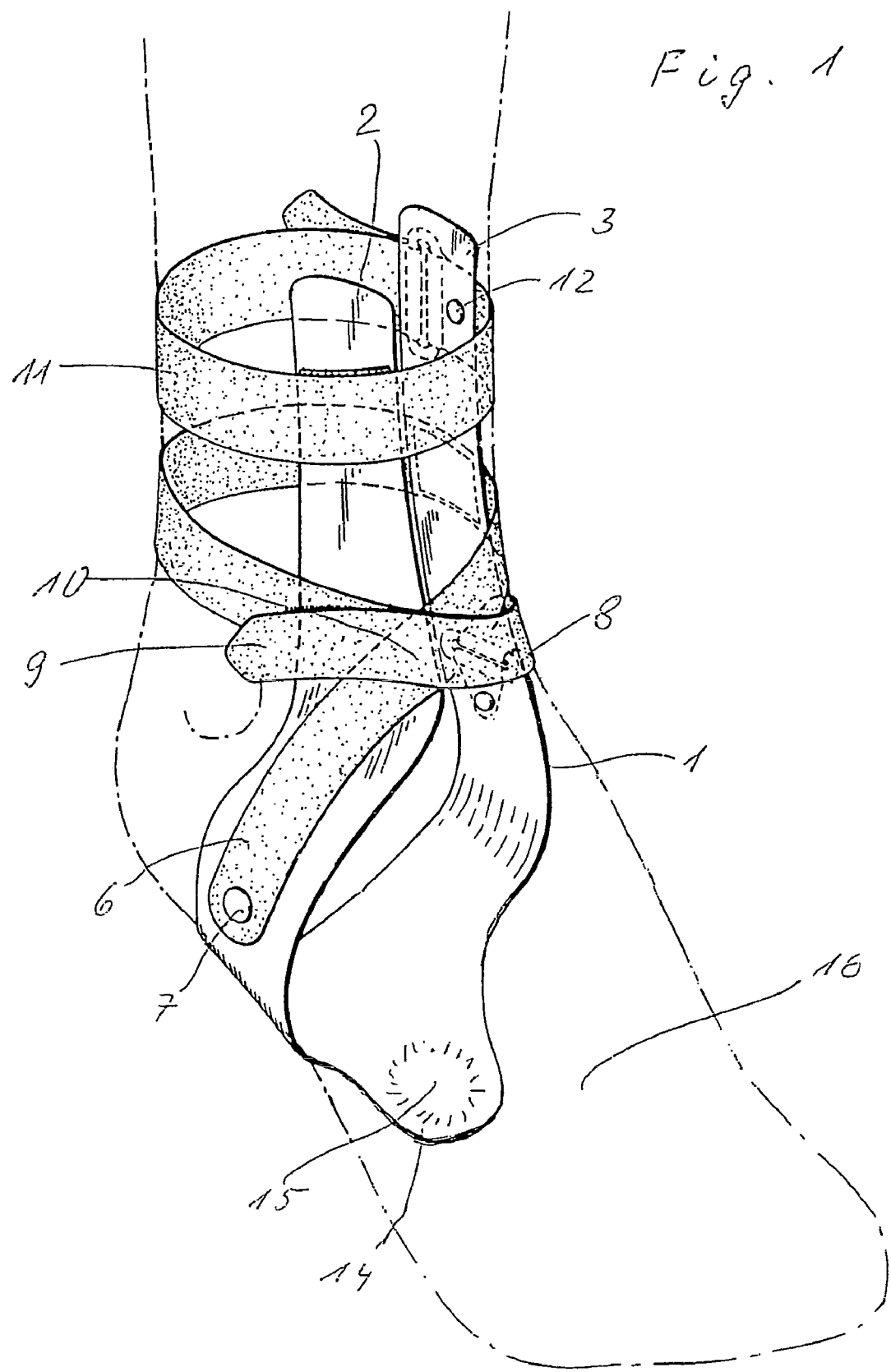

The invention relates to an ankle orthosis comprising a U-shaped support stirrup made of a flexible material, the sides of which stirrup converge beneath the foot in a web projecting as a tab toward the metatarsus, extend past the bones, and are held together at their end regions by a fastening strap wrapping around the leg. Such an orthosis is described in DE 41 12 069 A1. The design of this ankle orthosis serves to improve an ongoing healing process by enhancing its supportive action.

The object of the invention is to further improve the supportive action of the orthosis. According to the invention, this is accomplished by the means that the tab has a convex portion which bulges upwardly in a shape of a portion of a sphere, and presses against the cuboid bone of the foot due to a preloading of the tab.

This design of the inventive ankle orthosis takes advantage of an effect consisting in that areas exist in the sole of the foot that trigger reflex movements of the foot on account of pressure and corresponding transmission of a corresponding signal through the person's nerves, which reflex movements cause the foot to be largely brought into its normal position through muscle activity. The invention utilizes this effect by the means that, when pressure is applied to the cuboid bone, it triggers a signal in the applicable nerves of the foot, which results in involuntary adduction of the foot, thus moving the foot back to its normal position if applicable. During this process, tendons running in the vicinity of the cuboid bone are placed under tension, and thus accelerate corresponding activation of the associated muscles.

The tab can usefully be designed as a projection that extends from the web toward the forefoot along the outer side of the sole, terminates short of the metatarsus, and is flexible relative to the web. This design is particularly comfortable for the wearer of such an ankle orthosis, since the tab takes up only a small amount of space under the arch of the foot and thus is not perceived as a hindrance. It is useful to design the web and tab in such a manner that the two parts consist of different materials and have different elasticity.

An advantageous design of the web and tab can also be achieved in that the tab and the web are made as a single part, wherein the tab is weakened relative to the web. Such an embodiment can be accomplished in a single injection process, wherein a known and effective communication means can hence be chosen for the production of the ankle orthosis.

The acceptance of the ankle orthosis can be further improved in that the sides with the web and the tab are covered by a padding material on the side facing the body. In this case the ankle orthosis conforms to the wearer's leg and foot to a certain extent without the wearer feeling inconvenienced in any way by the ankle orthosis being worn.

So as to be able to adapt the ankle orthosis to feet of different widths, it is useful to design the web and sides such that the web extends far enough into the sides that its length can be matched to the foot width of the particular wearer by appropriately bending the web relative to the sides. When placing the ankle orthosis on a narrow foot the bend locations of the web then extend further into the sides, whereas the bend location moves more toward the web lying under the foot when placing the ankle orthosis on a wide foot.

In order to make the wearing of the ankle orthosis more comfortable, it is advantageous to design it such that a pad is provided on the inner surface of the outer side.

The figures depict an example embodiment of the invention. Shown are:

FIG. 1 the ankle orthosis placed on a foot;
FIG. 2 a view of the foot with the ankle orthosis from FIG. 1 in place, seen from the inner lateral side of the foot;
FIG. 3 a representation corresponding to FIG. 2 seen from the outer lateral side of the foot.

The ankle orthosis shown in FIG. 1 comprises the U-shaped support stirrup 1, which includes an outer lateral side 2, and inner lateral side 3, and the web 4 extending the wearer's foot for connecting the sides. A fastening strap 6 consisting of a hook and loop strap is attached to the lower region of the outer lateral side 2, being permanently attached to the outer lateral side 2 by the rivet 7 here. The fastening strap 6 is wrapped around the leg above the ankle, is passed back through a turn-around loop 8 shown with dashed lines (see FIG. 2), and extends with its end 9 past the crossing point 10 of the fastening strap 6, where it is pressed against the fastening strap 6 and held by the same in the manner of a hook and loop closure. In addition, the ankle orthosis has the fastening strap 11, which encloses the leg above the ankle and is fastened at one of its ends to the inner lateral side 3 by means of the rivet 12. The other end 13 of the fastening strap 11 is then pressed against this end and forms a hook and loop closure at the pressure point, where it is held in place after wrapping around the upper ends of the two lateral sides 2 and 3. This method of attachment of the U-shaped support stirrup 1 is a prior art design such as is known from the aforementioned DE 41 12 069 A1.

The web 4 has the tab 14 pointing towards the toes. Tab 14 includes a convex portion 15 which bulges upwardly in a shape of a portion of a sphere in the region of the cuboid bone of the ankle support wearer's foot, the tab being preloaded so that the convex portion 15 bulges upwardly in the direction of the cuboid bone and presses against and under side of the cuboid bone. The position of the tab 14 is chosen such that it is formed as a projection that extends under a portion of a sole the foot adjacent to the outer lateral side 2 of foot, which terminates before the metatarsus and is flexible relative to the web 4. The metatarsus is indicated here by dashed lines with respect to its outline, the region of the metatarsus is labeled with reference number 16. The effect explained in the above introduction is triggered by the convex portion 15 described above, causing a corresponding alignment of the ankle support wearer's foot.

The ankle support from FIG. 1 placed on the foot is shown in FIG. 2, with the direction of view being towards the inside of the foot. FIG. 2 shows the inner side 3 of the ankle support and the web 4, which is adjoined by the tab 14. The tab 14 becomes steadily thicker with increasing distance from the web, in this way achieving the desired pressure on the cuboid bone of the foot. FIG. 2 also shows that each of sides 2, 3, the web 4, and the tab 14 of the ankle orthosis is covered by a padding material 19 on the side facing the body FIG. 3 shows a representation of the ankle orthosis placed on the foot, with the direction of view being towards the outside of the foot. In this direction of view, the tab 14 is visible with thickness increasing towards the toes, by which means the desired pressure on the cuboid bone is achieved. It should also be noted with respect to FIG. 3 that the side 2 is shown somewhat broadened at its upper end in this depiction, which represents a certain deviation from the representation in FIG. 1. This broadening of the end of the side 2 makes wearing the ankle orthosis on the foot more comfortable. FIG. 3 shows that each of sides 2, 3, the web 4, and the tab 14 of the orthosis is covered by a padding material 19 on the side facing the body, and that a pad 18 is provided on an inner surface of the outer lateral side of the orthosis.

What is claimed is:

1. An ankle orthosis, comprising:
a U-shaped support stirrup for a user's foot made of a flexible material, and including inner and outer lateral sides which converge beneath the foot in a web, and a tab projecting forwardly from the web under the user's foot toward a metatarsus of the foot, and
a pair of fastening straps wrapping the support stirrup against a leg of the user,
wherein a portion of the tab adjacent to the outer lateral side of the support stirrup has a convex portion bulging upwardly in a shape of a portion of a sphere which presses against an underside of a cuboid bone of the foot due to a preloading of the tab.

2. The ankle orthosis according to claim 1, wherein the tab is formed as a projection that extends toward a forefoot only under a portion of a sole of the user's foot which is adjacent to the outer lateral side of the support stirrup, terminates short of the metatarsus, and is flexible relative to the web.

3. The ankle orthosis according to claim 2, wherein the tab and the web are made of different materials with different elasticity.

4. The ankle orthosis according to claim 2, wherein the tab and the web are made as a single part, the tab is weakened relative to the web.

5. The ankle orthosis according to claim 2, wherein each of the inner and outer lateral sides, the web, and the tab of the support stirrup has an inner side facing a body of the user that is covered by a padding material.

6. The ankle orthosis according to claim 2, wherein the web has a length which extends far enough into the inner and outer lateral sides of the support stirrup so that the length is capable of being matched to a width of the foot of a particular user by bending the web relative to the inner and outer lateral sides.

7. The ankle orthosis according to claim 2, wherein a pad is provided on an inner surface of the outer lateral side of the support stirrup.

8. The ankle orthosis according to claim 1, wherein the tab and the web of the support stirrup are made of different materials with different elasticity.

9. The ankle orthosis according to claim 8, wherein the web has a length which extends far enough into the inner and outer lateral sides of the support stirrup so that the length is capable of being matched to a width of the foot of a particular user by bending the web relative to the inner and outer lateral sides.

10. The ankle orthosis according to claim 1, wherein the tab and the web are made as a single part, and the tab is weakened relative to the web.

11. The ankle orthosis according to claim 1, wherein each of the inner and outer lateral sides, the web, and the tab of the support stirrup has an inner side facing a body of the user that is covered by a padding material.

12. The ankle orthosis according to claim 1, wherein the web has a length which extends far enough into the inner and outer lateral sides of the support stirrup so that the length is capable of being matched to a width of the foot of a particular user by bending the web relative to the inner and outer lateral sides.

13. The ankle orthosis according to claim 1, wherein a pad is provided on an inner surface of the outer lateral side of the support stirrup.

14. The ankle orthosis according to claim 13, wherein one of the fastening straps is attached at a lower portion of the outer lateral side of the support stirrup, and wraps around the leg of the user in a manner so as to overlap a portion of the outer lateral side where the pad is provided.

15. The ankle orthosis according to claim 1, wherein one of the fastening straps is attached to the support stirrup by a fastener located at a lower portion of the outer lateral side of the support stirrup.

16. The ankle orthosis according to claim 1, wherein the inner and outer lateral sides of the support stirrup have different shapes.

17. The ankle orthosis according to claim 1, wherein the tab is steadily thicker with increasing distance from the web, and thus is capable of providing a desired pressure on the cuboid bone of the foot.

* * * * *